United States Patent [19]

Bradley

[11] Patent Number: 5,081,011

[45] Date of Patent: Jan. 14, 1992

[54] METHOD AND TEST KIT FOR DETECTING INHERITED SUBSTANCE ABUSE DEPENDENCY

[75] Inventor: Ronald H. Bradley, Williamston, Mich.

[73] Assignee: Board of Trustees operating Michigan State University, East Lansing, Mich.

[21] Appl. No.: 470,772

[22] Filed: Jan. 26, 1990

[51] Int. Cl.$^5$ .................................. G01N 33/577
[52] U.S. Cl. ........................ 435/7.24; 435/30; 435/34; 436/548; 436/811; 436/901; 935/110
[58] Field of Search ................ 435/7, 30, 34, 435/7.24, 7; 436/548, 811, 901; 935/110

[56] References Cited

U.S. PATENT DOCUMENTS 4,361,550 11/1982 Kung et al. .................. 435/948

OTHER PUBLICATIONS

Bagasra et al., *Immunology*, 61, 63-69, 1987.
Coulter Immunology catalogue, Mar. 1989, p. 12.
Ford, In Weir (ed.), *Handbook of Experimental Immunology*, 3rd ed., Blackwell Scientific Publications, Oxford, 1978, pp. 23.6-23.7.
Johnson et al., In Weir (Ed.), ibid, pp. 15.5-15.6 and 15.16-15.17.
Mufti et al., *Immunopharmacology*, 15, 85-94, 1988.
Pelletier et al., *Gastroenterol. Clin. Biol.*, 8, 911-914, 1984.
Perrin et al., *Gastroenterol. Clin. Biol.*, 8, 907-910, 1984.
Vetter et al., *Gastroenterol. Clin. Biol.*, 11, 790-794, 1987.
J. W. Kimball, *Introduction to Immunology*, Macmillan Publishing Co., Inc., New York, 1983, pp. 141 and 147.
Diagnostic and Statistical Manual of Mental Disorders (Third Edition Revised), DSM-111-R, American Psychiatric Association, Washington, DC, 1987, pp. 167-169 and 346-347.
MacGregor, R. R.: "Alcohol and Immune Disease", JAMA 256:1474-1479, 1986.
Meyer, R. E., Dranzler, H. R.: "Alcoholism: Clinical Implications of Recent Research", J. Clin. Psychiatry 49:8-12, 1988.
Regan, T. J.: "Alcohol and the Cardiovascular System", JAMA 264:377-381, 1990.
Stoudemire, A., Thompson, T. L.: "The Borderline Personality in the Medical Setting", Annals of Internal Medicine 96:76-79, 1982.
Vaglum, S.: "Borderline and Other Mental Disorders in Alcoholic Female Psychiatric Patients: A Case Control Study", Psychopathology 18:50-60, 1985.
Watson, R. R., Mohs, M. E., Eskelson, C., Sampliner, R. E., Hartmann, B.: "Identification of Alcohol Abuse and Alcoholism with Biological Parameters", Alcoholism: Clinical and Experimental Research 10:364-385, 1986.
Cadoret, R. J., Troughton, E., O'Gorman, T. W., Heywood, E.: "An Adoption Study of Genetic and Environmental Factors in Drug Abuse", Arch. Gen. Psychiatry 43:1131-1136, 1986.
Cadoret, R. J., Troughton, E., O'Gorman, T. W.: "Genetic and Environmental Factors in Alcohol Abuse and Antisocial Personality", Journal of Studies on Alcohol 48:1-8, 1987.
Corsico, R., Pession, O. L., Morales, V., Jmelninsky, A.: "Association of HLA Antigens with Alcoholic Disease", Journal of Studies on Alcohol 49:546-550, 1988.
Goodwin, D. W.: "The Genetics of Alcoholism", Hospital and Community Psychiatry 34:1031-1034, 1983.
Goodwin, D. W.: "Studies of Familial Alcoholism: A Review", J. Clin. Psychiatry 45:14-17, 1984.

(List continued on next page.)

*Primary Examiner*—David Saunders
*Attorney, Agent, or Firm*—Ian C. McLeod

[57] ABSTRACT

A method and test kit for detecting and treating inherited substance abuse dependency by counting viable T-cell suppressor cells (CD8) is described. In the preferred form the T-cell suppressor cells are isolated and then counted. The method and test kit are important for distinguishing a genetic deficiency with a tendency towards alcoholism as opposed to a psychological dependency on drugs.

9 Claims, 7 Drawing Sheets

OTHER PUBLICATIONS

Guebaly, N.: "Risk Research in Affective Disorders and Alcoholism: Epidemiological Surveys and Trait Markers", Can. J. Psychiatry 31:352–360, 1986, May.

Gurling, H. M. D., Phil, M., Grant, S., Dangl, J.: "The Genetic and Cultural Transmission of Alcohol Use, Alcoholism, Cigarette Smoking and Coffee Drinking: A Review and and Example Using Log Linear Cultural Transmission Model", British Journal of Addiction 80:269–279, 1985.

Merikangas, K. R., Weissman, M. M., Prusoff, B. A., Pauls, D. L., Leckman, J. F.: "Depressives with Secondary Alcoholism: Psychiatric Disorders in Offspring", Journal of Studies on Alcohol 46:199–204, 1985.

Merikangas, K. R., Weissman, M. M. Prusoff, B. A., John, K.: "Assortative Mating and Affective Disorders: Psychopathology in Offspring", Psychiatry 51:48–57, 1988, Feb.

Parker, D. A., Harford, T. C.: "Alcohol-Related Problems of Children of Heavy-Drinking Parents", Journal of Studies on Alcohol 48:265–268, 1987.

Roosa, M. W., Sandler, I. N., Gehring, M., Beals, J., Cappo, L.: "The Children of Alcoholics Life-Events Schedule: A Stress Scale for Children of Alcohol-Abusing Parents", Journal of Studies on Alcohol 49:422–429, 1988.

Schuckit, M. A.: "Genetics and the Risk for Alcoholism", JAMA 245:2614–2617, 1985.

Schuckit, M. A., Gold, E. O., Croot, K., Finn, P., Polich, J.: "P300 Latency After Ethanol Ingestion in Sons of Alcoholics and in Controls", Biol. Psychiatry 24:310–315, 1988.

Schuckit, M. A.: "Two Decades of Alcoholism Genetics Research Reviewed", The Psychiatric Times * Medicine and Behavior :39–40, 1990, Feb.

Searles, J. S.: "The Role of Genetics in the Pathogenesis of Alcoholism", Journal of Abnormal Behavior 97:153–167) 1988.

Tanna, V. L., Wilson, A. F., Winokur, G., Elston, R. C.: "Possible Linkage Between Alcoholism and Esterase-D", Journal of Studies on Alcohol 49:472–476, 1988.

Tartar, R., Jacob, T., Bremer, D.: "Specific Cognitive Impairment in Sons of Early Onset Alcoholics", Alcoholism: Clinical and Experimental Research 13:786–789) 1989.

Tarter, R. E., Aalterman, A. I., Edwards, K. L.: "Vulnerability to Alcoholism in Men: A Behavior-Genetic Perspective", Journal of Studies on Alcohol 46:329–352, 1985.

Tarter, R. E.: "Are There Inherited Behavioral Traits That Predispose to Substance Abuse?", Journal of Consulting and Clinical Psychology 56:189–196, 1988.

Whipple, S. C., Parker, E. S., Noble, E. P.: "An Atypical Neurocognitive Profile in Alcoholic Fathers and Their Sons", Journal of Studies on Alcohol 49:240–244, 1988.

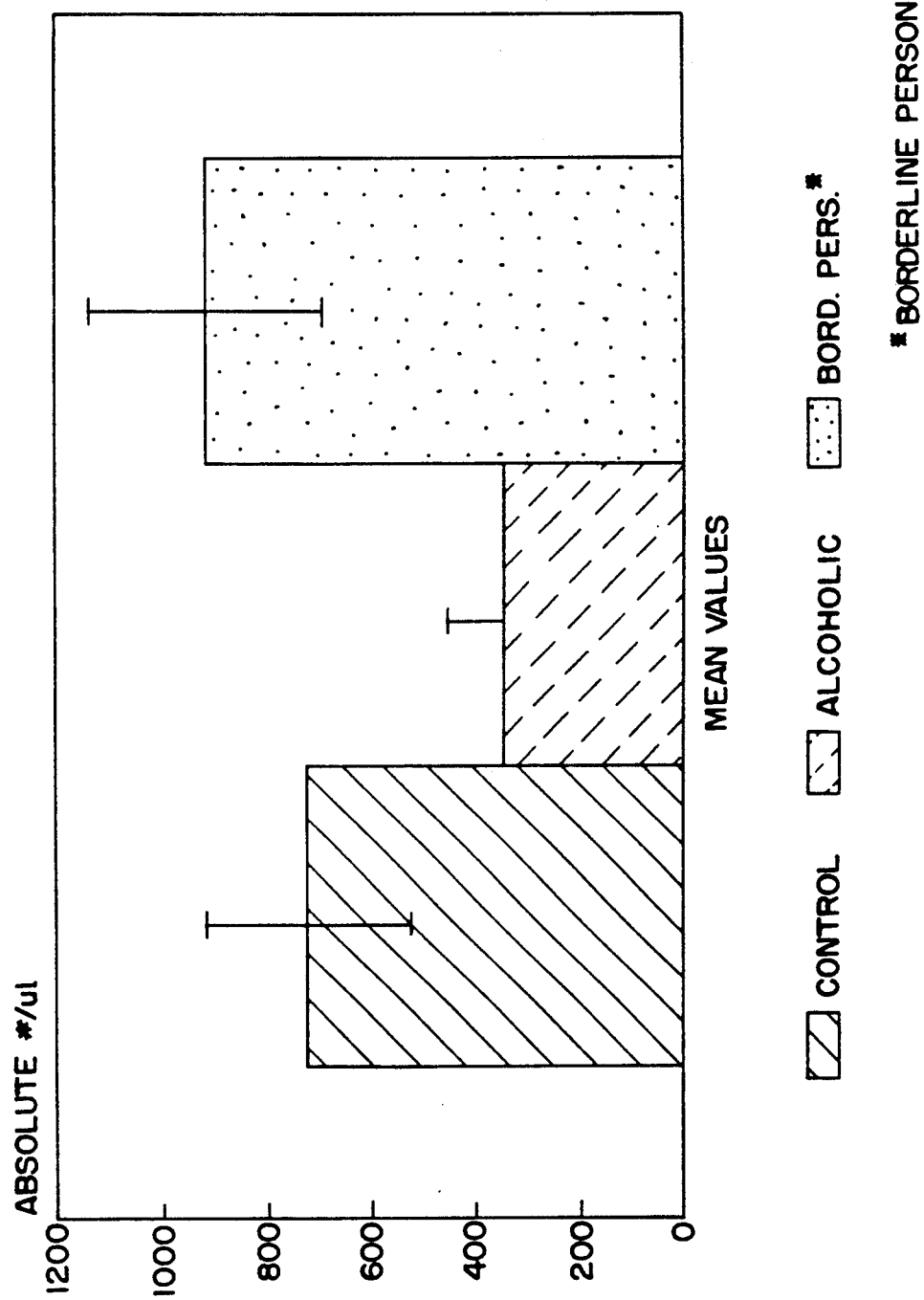

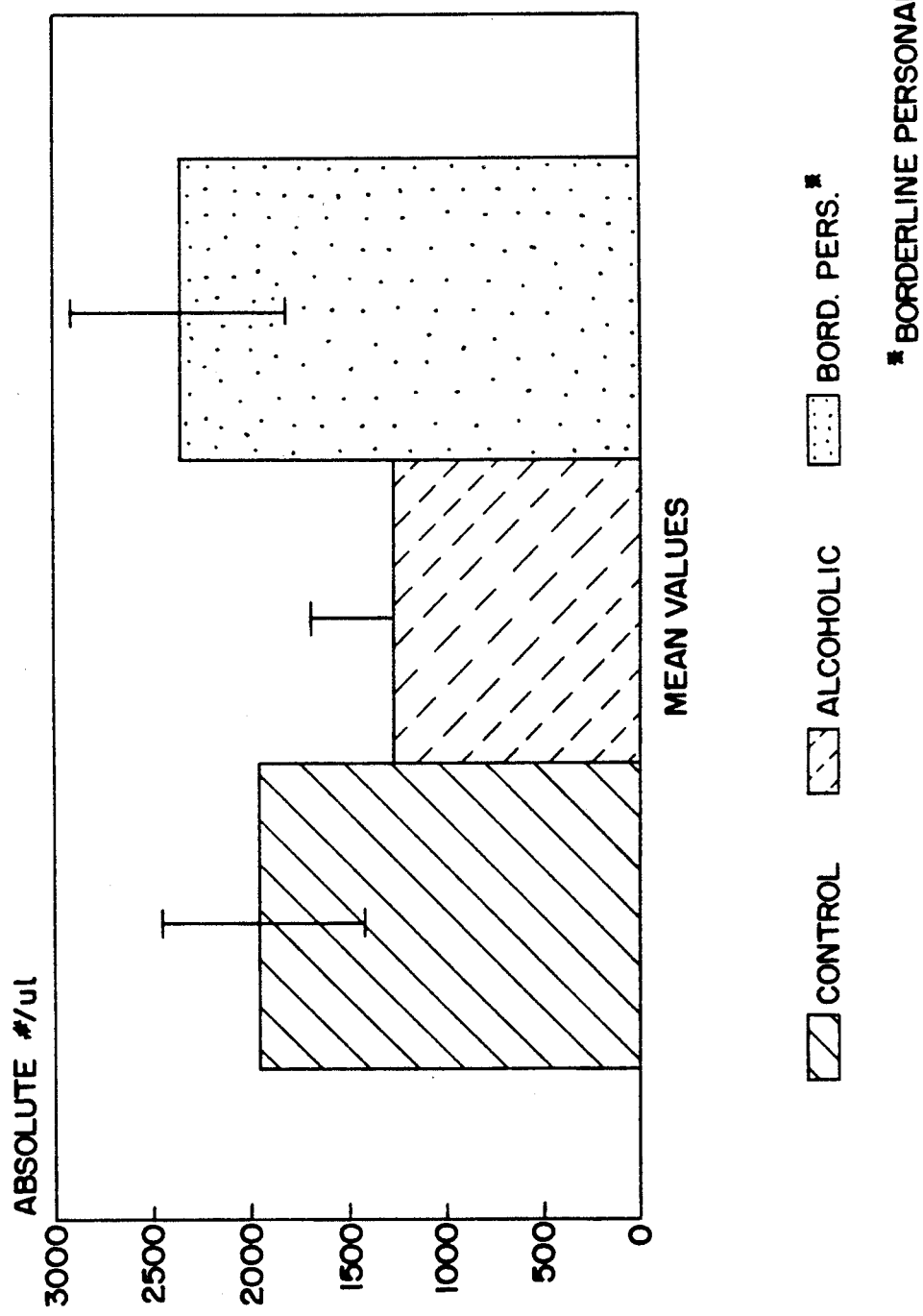

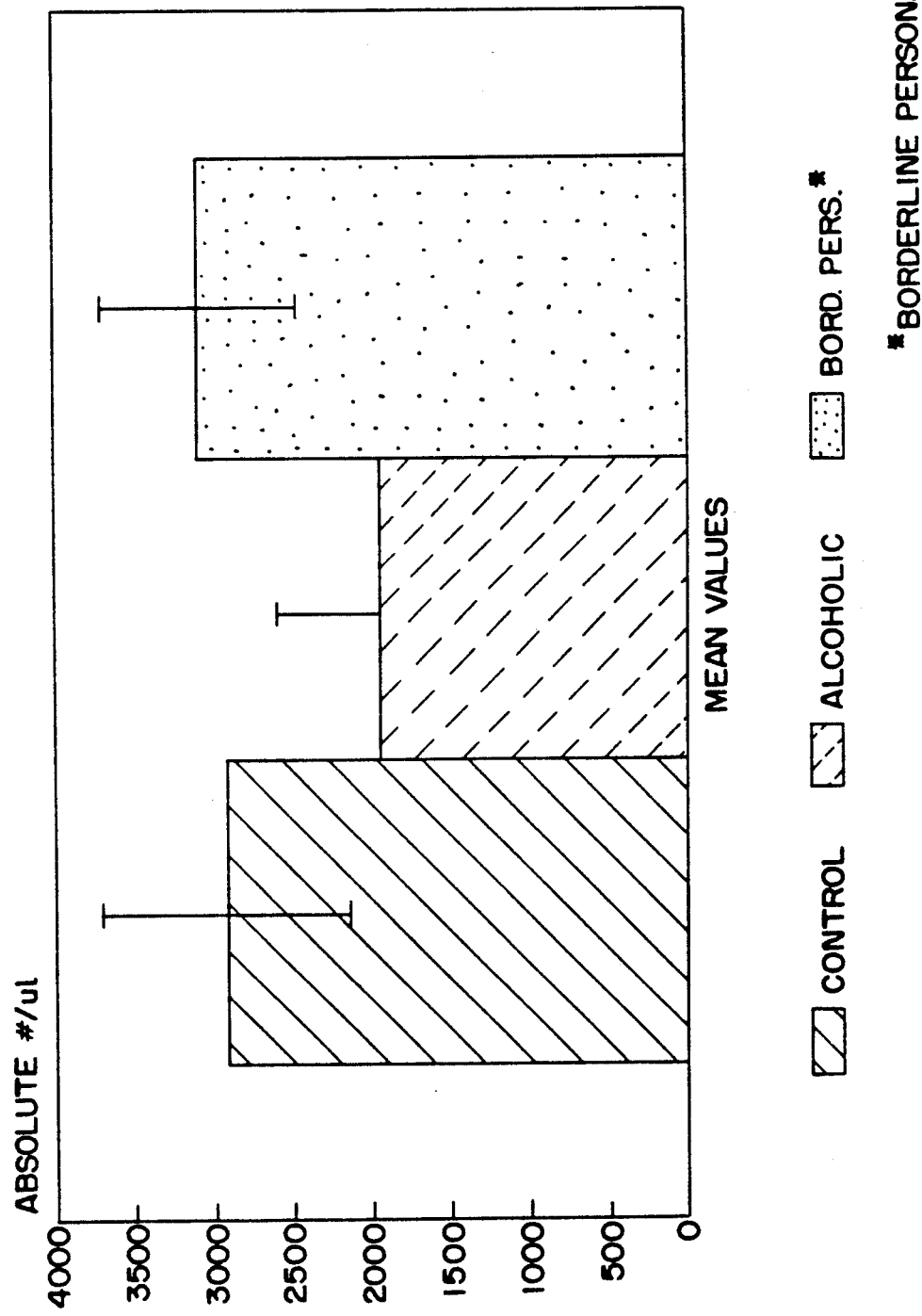

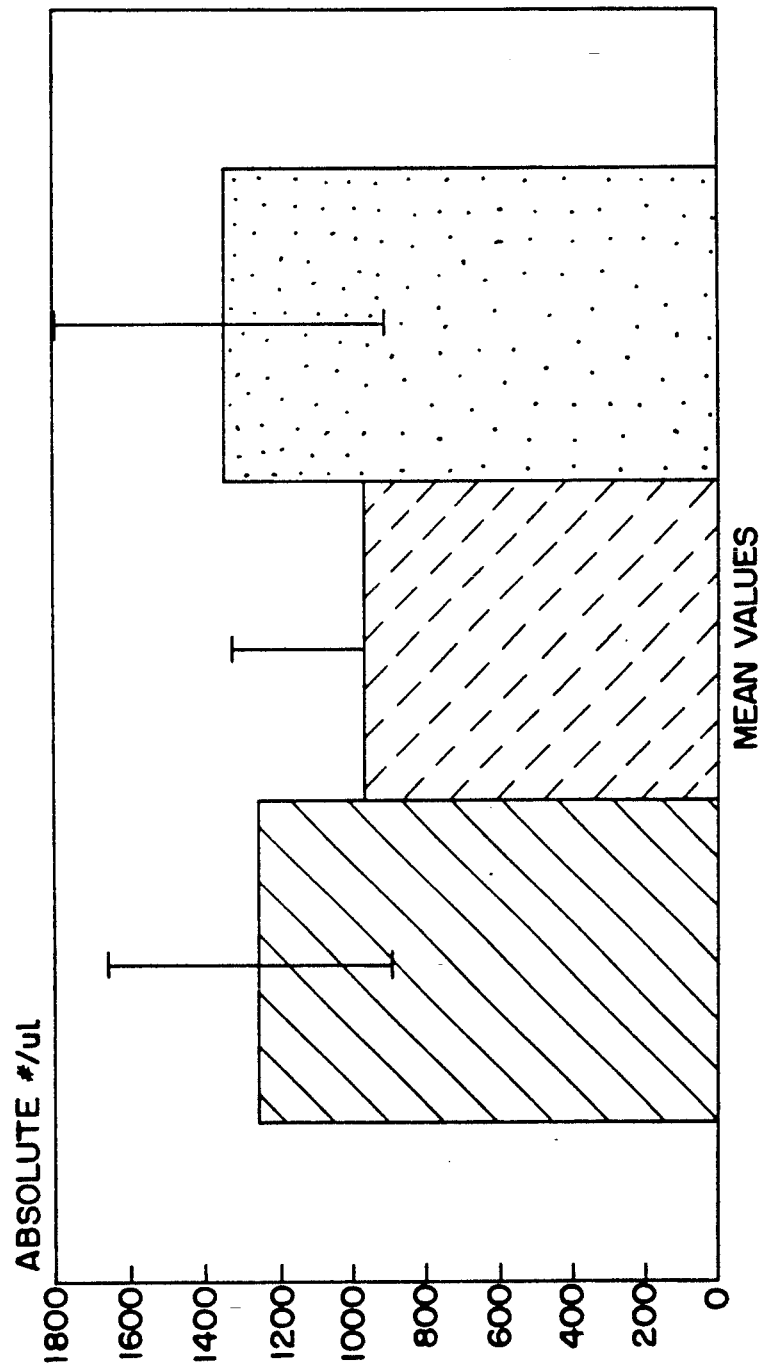

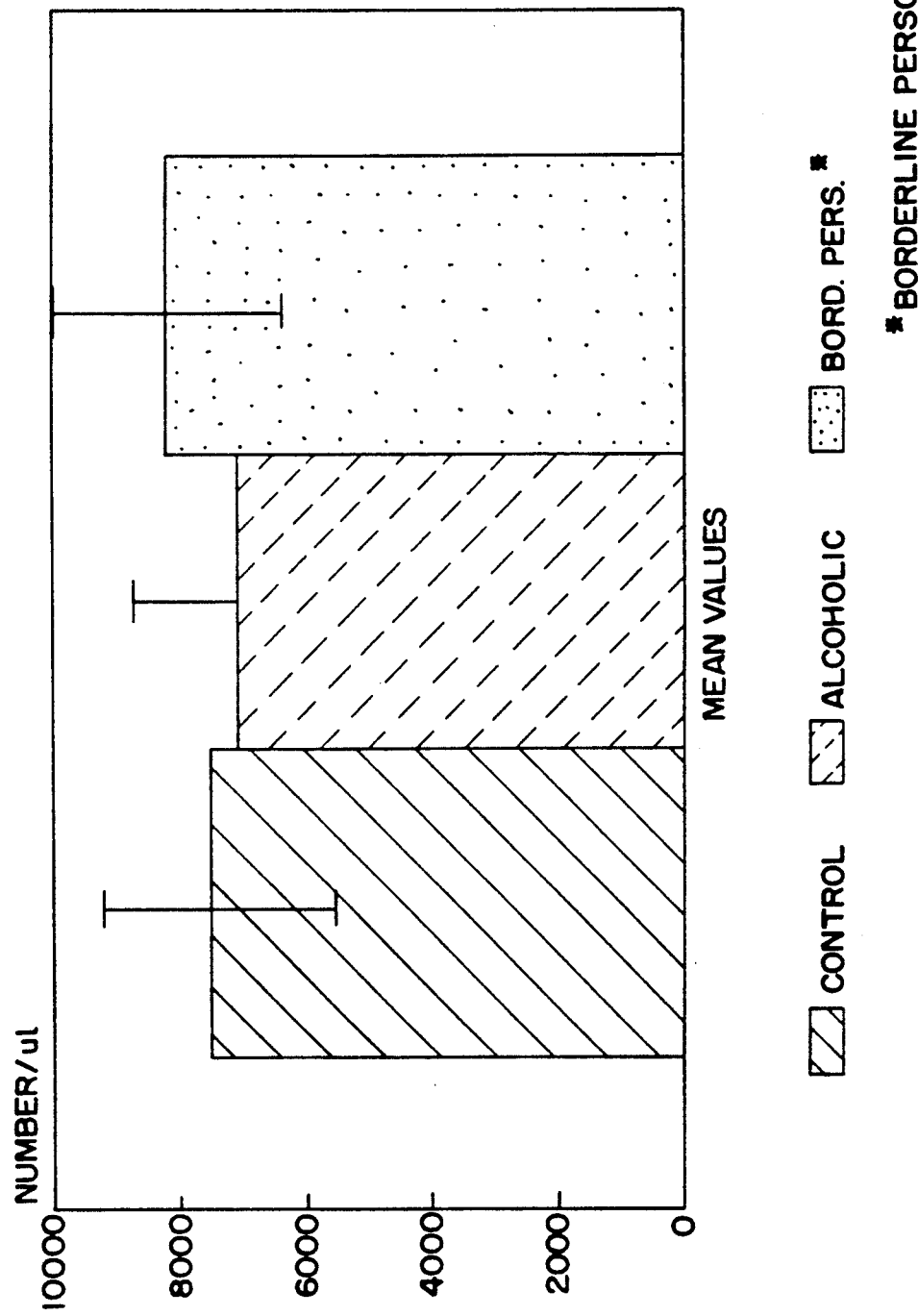

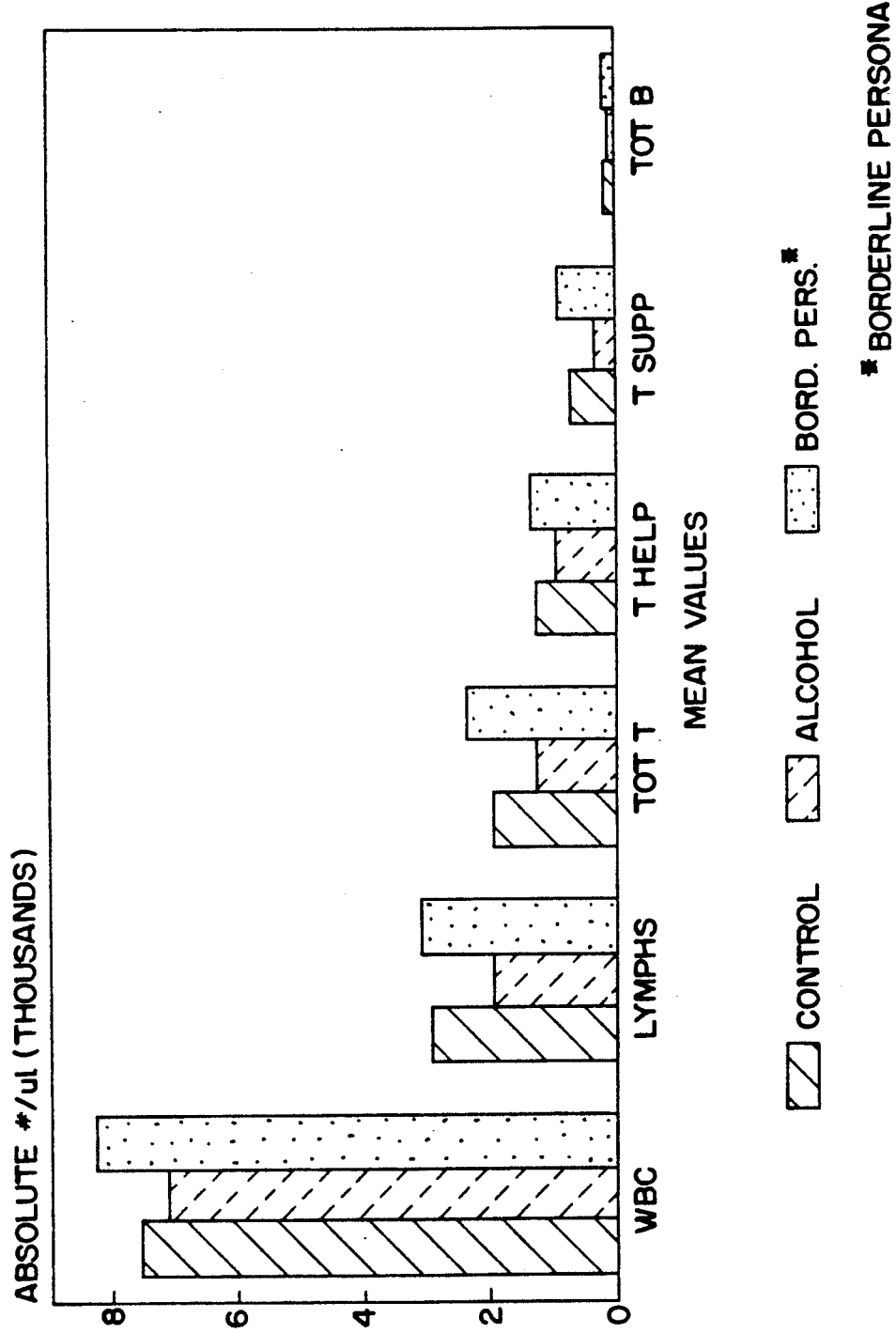

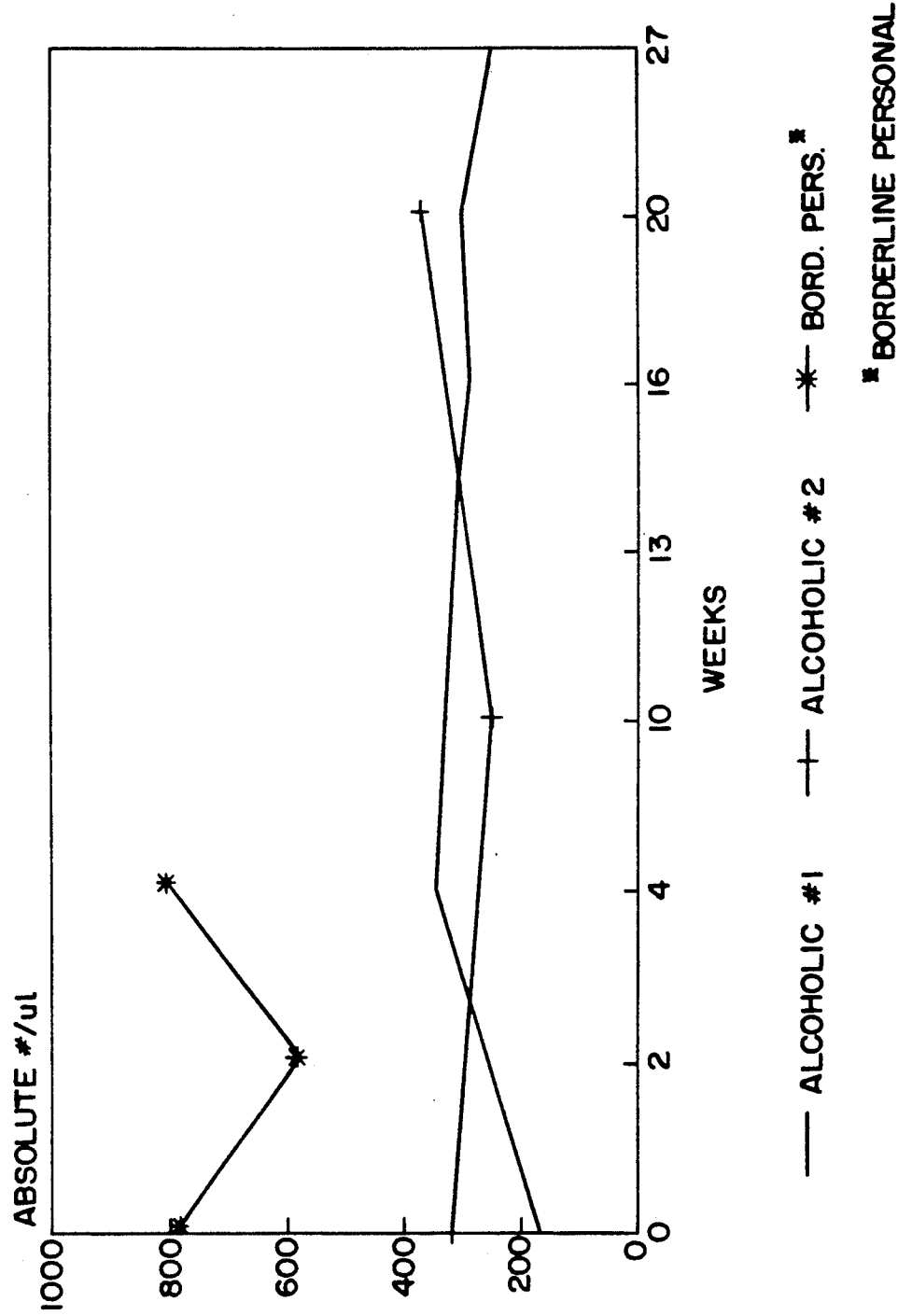

METHOD AND TEST KIT FOR DETECTING INHERITED SUBSTANCE ABUSE DEPENDENCY

BACKGROUND OF THE INVENTION (1) Field of the Invention

The present invention relates to a method and test kit for the diagnosis of an inherited substance abuse dependency in humans as a basis for subsequent treatment. In particular, the present invention relates to a method and test kit which detects low levels of lymphocyte T-cell suppressor cells (CD8) as evidence of the inherited substance abuse trait.

(2) Prior Art

The use and abuse of alcohol and other mind altering drugs which can be coupled with chemical dependency is a very serious problem. Alcoholism and mixed chemical dependency of alcohol with other drugs is a major concern of the health care system. It is a major concern of the gross national indebtedness of the U.S.A. with estimates ranging from $116 billion annual loss in manpower to $125 billion of the national health care cost. This is a total cost of over $200 billion being lost due to a disease called "alcoholism". The range of the economic consequences of alcoholism is felt on the industrial line, through airplane accidents, motor vehicle accidents, and from major oil spills to legislative leaders who are intoxicated or who deny that they have any problem, and various professionals. Political leaders are using the only problem-solving tactic known to them, which is to eliminate a very small portion of the problem through the "drug wars".

In the hospitals the costs of alcoholism is seen in the number of patient beds occupied by medical side effects of alcoholism. These side effects of alcoholism (whether it is acute or chronic) are an increased incidence of lung cancer, prostatic cancer, HIV (AIDS) syndromes, and other immunological and end organ consequences of ethanol toxicity.

A biological screen for alcoholism has been sought after for many years. In fact, the psychosocial and psychobiological understanding of the alcoholic patient has been a great mystery to man for at least 2,000 years. Today in modern society little is known about how a person may become an alcoholic, although, as mandated by a recent United States Supreme Court landmark case, it is strongly suggested that the behavior of an individual is the only key consideration as to whether a person will develop alcoholism; that is, it is not a disease state which is incorrect in many instances.

There have been numerous individuals and institutions who have devoted their lives to an attempt to understand this complex phenomenology. One approach which suggests that male children who are "role modeled" in a dysfunctional family are at higher risk to develop alcoholism than the average population if their fathers are alcoholic. This type of family dynamic leads one to understand that these children are felt in their own words to be abandoned, lost, neglected, appear to suffer from early deprivation of parental role modeling, and therefore are more likely to suffer from personality disorders that can become true psychopathological manifestations. It is this type of person who utilizes alcohol as a means to control the anger within towards the object relationships that so greatly disappoint them. This disappointment then leads to alcohol (an anesthetic drug) being used to soothe the pain of anger and punishment that they feel when they cannot achieve their high expected goals for the love, understanding, and nurturing that they did not receive as a child. Now as adults they are desperately looking for the parent that was not there for them. There is a strange reversal in this type of alcoholic personality which allows another close-loved human (the "enabler") to be used as a vehicle for the patient's own self destruction and eventual failure, the same treatment as they had received so many other times in their lives.

There is another type of alcoholic that cannot stop at "one drink" and who in the past has been referred to by several investigators as a "gamma drinker". These people may go long periods between the "binges", but when it starts they cannot stop drinking and/or substance abuse. This type of client will do anything to get alcohol/mixed chemical dependency pharmaceuticals. They even steal doctor's prescription pads or steal D.E.A. numbers to obtain their own medications in order to further the disease.

There are two types of substance dependence/abuse patients. As outlined by Diagnostic Statistical Manual Version III-R (DSM III-R), Psychoactive Substance Dependence requires at least three of the following criteria: 1. Substance often taken in larger amounts or over a longer period than the person intended; 2. Persistent desire or one or more unsuccessful efforts to cut down or control substance use; 3. A great deal of time spent in activities necessary to get the substance, taking the substance or recovering from its effect; 4. Frequent intoxication or withdrawal symptoms when expected to fulfill major role obligations at work, school, or home; 5. Important social, occupational, or recreational activities given up or reduced because of substance use; 6. Continued substance use despite knowledge of having a persistent or recurrent social, psychological, or physical problem that is caused or exacerbated by the use of the substance; 7. Marked tolerance: need for markedly increased amounts of the substance in order to achieve intoxication or desired effect; 8. Characteristic withdrawal syndromes; 9. Substance often taken to relieve or void withdrawal syndromes.

Psychoactive Substance Abuse is a separate category which is a residual category for noting "maladaptive patterns of psychoactive substance use." Diagnostic criteria for this as outlined in DSM III-R are: 1. A maladaptive pattern of substance use indicated by at least one of the following: a. Continued use despite knowledge of having a persistent or recurrent social, occupational, psychological, or physical problem that is caused or exacerbated by use of the psychoactive substance; b. Recurrent use in situations in which use is physically hazardous; 2. Some symptoms of the disturbance have persisted for at least one month, or have occurred repeatedly over a longer period of time; 3. Never met the criteria for Psychoactive Substance Dependence for this substance.

There appears to be a combination of the two alcoholic schemata which presents with a criteria as outlined in DSM III-R, referred to as Axis I diagnosis of alcohol abuse and/or dependency combined with an Axis II diagnosis of personality disorder (which includes primarily borderline personality, antisocial personality and narcissistic personality). These Axis II personality disorders have been thought of as temperament. This temperament, (some say we are born with these characteristics), is the phenotypic expression of one's own genetic inheritance related to male dominance. This temperament, of an individual's nature, has been thought to be the underlying cause of alcoholism derived from the male parent's temperament/alcoholism. Many behavioral theorists have tried with limited success for the past 40 years to treat alcoholism/chemical dependency in this manner.

Today, from a psychiatric and neuro-cell-biological aspect, physicians are beginning to see a glimpse of the importance of the psychodynamic aspects of the alcoholic environment and its profound effect on the children of the future/today, but it also has clinical measurable aspects as a disease entity, alcoholism. Alcoholism is a disease, and it can no longer be defined as just bad behavior. The definition of disease from Webster's New World Dictionary states: "1. any departure from health; illness in general. 2. a particular process in an organism, with a specific cause and characteristic symptoms". This disease state can and does affect the entire family dynamics, as well as affect the alcoholic individual in a particular manner with a specific cause and characteristic symptoms. What has been so confusing in the aspect of alcoholism is the effect on our whole society. To deal with it as a disease would mean that we would have to look at almost every aspect of our lives intermingled with our family dynamics, from all socioeconomic strata including health care providers and the legislators/political leaders.

The only known prior art associating lymphocytes with characterization of disease states are McAllister et al, Arch Gen Psychiatry 46 890-894 (1989) and Schleifer et al, Arch Gen Psychiatry 46 81-87 (1989). They do not relate to T-cell suppressor cells (CD8) and are concerned with patients with mental disorders. The techniques described by these references can be used in the present invention.

OBJECTS

It is therefore an object of the present invention to provide a method and test kit for identifying an inherited substance abuse dependency. It is further an object of the present invention to provide a method and test kit which is simple and economical. These and other objects will become increasingly apparent by reference to the following description and the drawings.

IN THE DRAWINGS

FIG. 1 is a graph showing the results of Tables 1 to 3 for the T-cell suppressor cells.

FIG. 2 is a graph showing the total T-cells (T) in Tables 1 to 3 ($CD_4$, $CD_8$ and $CD_{19}$).

FIG. 3 is a graph showing the total lymphocytes AT in Tables 1 to 3.

FIG. 4 shows the T helper cells ($CD_4$) as shown in Tables 1 to 3.

FIG. 5 is a graph of the white blood cell count (WBC) as shown in Tables 1 to 3.

FIG. 6 shows a comparison of the various cell counts shown in Tables 1 to 3 and FIGS. 1 to 4.

FIG. 7 shows the average values of the T-suppressor cells over time in the patients.

GENERAL DESCRIPTION

The present invention relates to a method for diagnosing an inherited substance abuse dependency in humans which comprises: determining a number of T-cell suppressor cells in white cells in a human subject; and comparing the T-cell suppressor cells of the subject to the T-cell suppressor cells of a human without a substance abuse dependency and with normal numbers of T-cell suppressor cells to determine whether the human subject has a reduced T-cell suppressor cell number and thus the inherited substance abuse dependency.

The present invention further relates to a method for diagnosing an inherited substance abuse dependency in humans which comprises: drawing a sample of blood from the human; separating white cells from the blood containing T-cell lymphocytes including T-cell suppressor cells; and determining a number of the T-cell suppressor cells in the white cells wherein the human with the substance abuse dependency has a reduced T-cell suppressor cell number as compared to humans without the dependency.

The present invention also relates to a test kit for diagnosing an inherited substance abuse dependency in humans which comprises: an agent which enables the separation of mononuclear T-cell lymphocytes including T-cell suppressor cells from other cells in blood of the human; and a labeled antibody which selectively reacts with surface antigens of lysed T-cell suppressor cells; wherein in use of the kit the agent is used to separate the T-cell lymphocytes from the blood, and the labeled antibody reacts with the T-cell suppressor cells to provide labeled cells which are counted and then compared to humans without the substance abuse dependency.

The present invention further relates to a test kit for diagnosing an inherited substance abuse dependency in humans which comprises: a centrifuging agent which enables the separation of mononuclear T-cell lymphocytes including T-cell suppressor cells from other cells in blood of the human; a lysing agent for lysing an remaining of the other cells in the separated T-cell lymphocytes; and a labeled antibody which selectively reacts with surface antigens of the separated T-cell suppressor cells; wherein in use of the kit the centrifuging agent is used to separate the T-cell lymphocytes from the other cells, the lysing agent lyses- the other cells in the separated T-cell lymphocytes and the labeled antibody reacts with the T-cell suppressor cells to provide labeled cells which are counted and then compared to humans without the substance abuse dependency.

The present invention provides a basis for distinguishing between an inherited substance abuse dependency and a psychological dependency. It has been found that, of the persons tested including alcoholics and non-alcoholic dependents of alcoholics, about 50% have the inherited trait. The fact that it is inherited is evidenced by the tests on non-alcoholic dependents.

In the treatment of those persons with the inherited dependency, it has been found that once they understand that they have an inherited disease, the response to treatment is dynamically improved. Over a period of 6 to 12 months only 2% of these persons, all of whom were diagnosed as alcoholics, have gone back to drinking.

The present invention has the capability of screening individuals for the T-cell suppressor cell deficiency. Once these persons are warned of the potential for a problem it is much easier for them to avoid alcohol or other mind altering drugs.

The results presented herein are for alcoholism alone or usually combined with other drugs. Other substance abuse problems can be diagnosed in the same manner since the low level of T-cell suppressor cells is an indication of an inherited tendency to be addicted to other drugs. It may be that once a person understands that he or she has this inherited characteristic, the use of mind altering substances will be avoided.

It has been found that a normal T-cell suppressor cell number is above about 500 cells per microliter of the whole blood. An abnormal number is well below 500 cells per microliter of the whole blood. A borderline personality population is within normal limits and thus does not have the T-cell suppressor cell marker.

Preferably the antibody is labeled using fluorescein isothiocyanate. Other fluorescent labeling agents, such as phycobiliproteins, (e.g. phycoerythrin) can be covalently linked to the antibody which binds the T-cell suppressor cells. All of these labeling methods are very well known to those skilled in the art.

The T-suppressor cells can be determined by other than an antibody. Microscopic techniques can be used to count the cell numbers. Thus light microscopes and electron microscopes can be used.

It was found that 99% of the T-cell suppressor cells were viable in random testing. Thus it was not necessary to continuously test the T-cell suppressor cells for viability.

SPECIFIC DESCRIPTION

Example 1

Alcoholics in the age group between 20 to 40 year old and their aged matched-sex control patients were analyzed by a psychosocial questionnaire. Comparative blood analyses were also performed. Exclusion criteria were strictly enforced. Patients (either control or alcoholic) with abnormal SMAC's or liver infection (hepatitis A, B or non A-B) and HIV positive screens were not accepted for this experiment.

The results hereinafter show that there is significant variability in the human T-cell lymphocyte subset classified as the T-cell suppressor cell type referred to as the CD8 cell surface marker. The alcoholic and mixed drug dependent patients when compared to their aged-matched-sex control showed a significant deficiency in CD8. Analyses were carried out over a 25 week period for controls (non-alcoholic and nonmixed chemical dependency) and the percentage of CD8 cells (% CD8 cells to total lymphocytes) and total number of CD8 cells did not change. Alcoholism was associated with the CD8 cells, and there was a strong correlation between the psychosocial questionnaire and the biological test for CD8 lymphocytes with a Student's T test value $p=0.024$.

Non-alcoholic children of alcoholics in the pre-teens and early adolescence were examined and the same deficiency in the CD8-T-cell population was found whether it was in male or female offspring of the alcoholic parents.

MATERIAL AND METHODS

Patients and Controls

Patients (subjects) were selected from random populations of four principal sites; either St. Lawrence Unit B, Lansing, Mich. (general inpatient psychiatric unit), Lansing General Hospital, Lansing, Mich., (primary care hospital setting), Horizon Center (a Lansing, Michigan General Residential Substance Abuse Unit) or Outpatient Substance Abuse Clinic at Michigan State University, East Lansing, Mich. All facilities are located in a metropolitan area which consists of major automobile factories, the State Capital of Michigan, and a major Big Ten University setting.

Patients and their aged-sex-matched-controls were selected from the same metropolitan area. The ages of the patients and their controls were between 20 to 40 years old. DSM III-R criteria, set forth hereinafter, for alcohol dependency/abuse, cocaine dependency/abuse, marijuana dependency/abuse, benzodiazepine dependency/abuse, or any other encountered mixed chemical dependency/abuse were strictly used. The patients had to be free of any major psychiatric disorder on Axis I, i.e. major affective disorder, schizophrenia, anxiety disorder etc., in order to meet inclusion criteria.

Patients and their aged-sex-matched-controls had to be free of any medical illness which included influenza, upper respiratory infections, chest colds, cellulitis, gastrointestinal infection or illness and they had to be on no medications, including no birth control medications. Essentially, all research clients had to be free of all medications for at least 10 days and have no illness other than alcoholism. Alcoholic patients and their aged-sex-matched-controls were given a consent form for research to read and sign.

Patients and controls were then given a comprehensive physical examination, a detailed medical history, family genogram (including psychiatric and medical) for at least three generations and a diagnostic-research interview which includes an expansion and restructuring of the Michigan Alcohol Screening Test, Hamilton Depression Rating Scale, Live Stress Events Scale and complete psychiatric evaluation [mental status examination, cognitive testing, neurological examination, and nutritional screen, caffeine use and use of tobacco].

Patients and controls were drawn three tubes of blood (drawn between 7:30 a.m. and 11:00 a.m.) for the laboratory portion of the alcohol screening. The blood products tested are listed in the section labeled Laboratory Methods.

The patients and controls were drawn on three separate occasions: day 1, day 12 and day 144. Patients and their controls were analyzed using a soft-ware package "Systat TM" version 4.0 on an IBM-XT personal computer. Differences in psychobiological measures among the patients and their controls were by analysis of variance. Significant differences in stress and/or depression score emerged, and analysis of covariance with stress and/or mood states as covariables were also performed.

Characterization of CD8-T-cells

CD8-T-cells were identified by use of a common available monoclonal antibody to a CD8 lymphocyte surface antigen as a marker. Other commercially available lymphocyte antigens (antibodies) used were: Total T-cell—CD3, Total B Cells—CD19, T Helper Cells—CD4. These lymphocyte antigens were analyzed as per the procedure outlined above.

To prepare the monoclonal antibodies, the surface marker is isolated through PAGE-Electrophoresis of human peripheral blood acquired through vena-puncture usually of the median antecubital vein. The whole blood was isolated to white blood cells using Sepracell-MN (a colloidal silica based medium which forms a continuous density gradient by rapid centrifugation; Sepratech Corporation, Oklahoma City, Okla.). The cells are checked for viability using the Trypan Blue, exclusion method (Sigma Chemical Company, St. Louis, Miss.), counted and diluted to $2 \times 10^{-6}$ cells/ml in RPMI-1640 complete media supplemented with either 10% fetal calf serum or 2% autologous human serum. T-cells are then put into SDS-PAGE incubating buffer and applied to Neville system of PAGE-Electrophoresis on a discontinuous gradient. The cells are lysed and injected into mice and spleen cells are isolated and fused with a myeloma to produce a hybridoma. Monoclonal antibodies are raised in mouse hybridoma cell lines to T-cell surface marker.

Laboratory Methods

Blood samples were obtained from age/sex matched alcoholics and controls for the following tests: Complete Blood Count (including differential), Lymphocyte surface marker analysis (Total T-cell, Total B cell, T Helper and T Suppressor), Human Immunodeficiency Virus (HIV), Hepatitis B Surface Antigen ($HB_sAg$) and a standard chemistry profile (SMAC).

Testing for HIV and $HB_sAg$ was performed by the Michigan Department of Public Health. The chemistry profile (SMAC) was performed by a local reference laboratory using standardized methodology.

Commercially prepared conjugated monoclonal antibodies and Coulter lysing reagent (Coulter Electronics, Hialeah, Fla.) were used for the determination of the lymphocyte surface markers. Direct immunofluorescence cell surface staining following the manufacturers' instructions was performed on 100 $\mu$l of ACD whole blood using fluorescein isothiocyanate (FITC) or phycoerythrin (PE) conjugated murine monoclonal antibodies (Simultest TM Reagents-Becton-Dickinson, Mountain View, Calif.; Catalog Nos. 950008 or 7317).

The whole lymphocyte preparation was lysed with a lysing reagent (Coulter Electronics, Hialeah, Fla.) to lyse non-lymphatic cells which interfere with the staining. Thus all samples were incubated for 30 minutes, washed twice with PBS/azide to fix the cells, lysed and fixed (Coulter Clone ®/Coulter Electronics), washed 3 times with PBS/azide and refrigerated until analyzed. Other human or mammalian antibodies will also work.

The lymphocyte antigens investigated included: Total T-Cell—CD3, Total B-Cells—CD19, T Helper Cells $CD_4$ and T Suppressor Cells—CD8. The fixed cells were analyzed and quantitated on an Ortho Cytofluorgraph Flow Cytometer (Becton-Dickinson, Mountain View, Calif.) using a dual laser system.

A complete blood count (CBC) including differential was performed manually using standardized methods for WBC and RBC Hemoglobin Hematocrit and differential count.

Discussion

Using the DSM III-R criteria, psychoactive substance using patients were classified and diagnosed. All possessed a diagnosis of psychoactive substance dependency plus maladaptive patterns of psychoactive substance abuse/use since all these patients were in treatment programs or were hospitalized due to maladaptive behavioral patterns in society.

However, when these patients were evaluated using the Alcohol Screening Test of the present invention (significant low numbers of CD8 T-cell lymphocytes plus abnormal mitogen stimulation), there emerged two types of alcoholics. One had normal functioning CD8 s T-cell lymphocytes possessing within normal ranges above 500 cells per microliter of the blood CD8 T-cell lymphocytes (referred to as Gene Negative Psychoactive Substance Abuse), while the other had significantly lower numbers of CD8 s T-cell lymphocytes (less than 500 cells per microliter of the blood) with an abnormal mitogen stimulation test (referred to as Gene Positive Psychoactive substance dependency/abuse).

The Gene Negative Psychoactive Substance abuse patients all possessed strong Axis II—DSM III-R, Cluster B, personality disorders. The most notable personality disorders were of the three following: 1. Borderline Personality disorder; 2. Antisocial Personality Disorder; 3. Narcissistic Personality Disorder. Common emotional feelings among the three personality disorders were: 1. a feeling of rage/anger (unexplained); 2. A feeling of abandonment; 3. Pattern of irresponsible and antisocial behavior since the age of 15; 4. Affective instability; 5. Impulse to use a psychoactive substance to relieve any of the above feelings on an unconscious level in order to escape the feelings or to be punished for the anger/rage they feel; and, 6. Patients perceived that they were raised in a dysfunctional family dynamic.

The Gene Positive Psychoactive Substance Dependency/abuse patients all had the following common patterns of dependency/abuse patterns: 1. They started abusing alcohol at a younger age grouping than Gene Negative patients, ages 8-15 with man age of 13; 2. Possessed at least three generations of alcoholism in their family genogram; 3. Were dynamically raised in a dysfunctional family (as opposed to Gene Negative, they had extremely poor parenting due to Psychoactive Substance Dependency primary objects or paternal object non-relationships); and 4. Psychoactive substance abuse was a normal occurrence in the family dynamics (i.e.—it was normal for parents to cope with psychoactive substances).

The laboratory results are shown in Tables 1 to 3 and FIGS. 1 to 7 indicate lymphocyte functioning in the three groups: Gene Positive Psychoactive Dependency Patients, their aged-matched-sex controls, and the Gene Negative Psychoactive Dependency/Abuse Patients. The Gene Positive Psychoactive Substance Dependency/abuse patients possessed a significantly lower number of CD8 T-cells. The CD8 T-cells of these patients are unable to suppress total lymphocyte growth, whereas the Gene Negative Psychoactive Dependency/Abuse patients and the aged-matched-sex controls possessed an ability to suppress total lymphocyte growth.

Data analyzed from the psychosocial questionnaire and laboratory CD8 T-cell lymphocyte studies of four, two generation studies (which are included in Table 2 (Cases 78) indicate that it is necessary for the mother to be Gene Positive Psychoactive Substance Dependency/abuse for their offspring (youngest age tested—2) to possess the identical Gene Positive Profile, i.e.—CD8 T-cell lymphocytes to be significantly lower (p—0.024).

The results in Example 1 show a genetic linkage to a disease state called "Alcoholism" and a behavioral Psychoactive Dependency/Abuse patient. The Gene Positive Psychoactive Substance Dependency/Abuse patient is in all likelihood what used to be called the "alcoholic". It is this type of patient who biologically has no control of his/her own disease state, just as diabetics know that sugar is not healthy for them, but still like eating "sweets". In this case the "sweets" are Psychoactive Substances that have profound, long lasting and unforgiveable effects on the entire body. These effects include: inflammation of the liver, the brain, the kidneys, and the lungs due to the toxins of Psychoactive Substances when metabolized in the organs. What we cannot measure is the damage the Psychoactive Substances have on a patient's interpersonal relationships. These relationships include parenting, being an offspring in this diseased family in denial, occupational problem-relationships, social, and net productivity of these diseased individuals.

Example 1 shows that alcoholism disease is not being treated properly or even diagnosed. The assumption is that if we just get rid of the Psychoactive Substances, the disease will go away. This very approach was tried in the 1920's with Prohibition, and if history is indeed repeated, the disease will not disappear. The disease, illness, a flight from health, will not be treated. The disease of "Alcoholism", "Psychoactive substance Dependency/Abuse" will not be diagnosed and/or treated.

The results of the test of the present invention is that there is a significant disease that is being transmitted and nurtured in America. The high risk which the diseased individuals have to other biological illness is overwhelming. CD8 T-cell lymphocytes are indeed labeled T cytotoxic/suppressor cell type. The exact function of the CD8 T-cell is still under investigation, but it appears that if one possesses a chronic low number of CD8 non-functioning cell types, that an individual would be susceptible to viral infections, sepsis from bacterial toxins and even the inability to recognize self. Thus the "Alcoholic" diseased, Gene Positive Psychoactive Substance Dependency/Abuse patient is at a great risk for HIV infection, Hepatitis A, B and non A/B as well as lung cancer, due to the fact that many "Alcoholics" smoke tobacco.

Thus, "Alcoholism", i.e. Psychoactive Substance Dependency/Abuse patients can be successfully diagnosed with the test for CD8 T-cell numbers and the function of these cells within a total population of lymphocytes. It has been found that there are two types of "Alcoholics"/Psychoactive Substance Dependency/Abuse patients by using this test kit. Diagnosis, treatment and overall relapse of these Gene Positive diseased patients with this kit have shown dramatic improvements over a year period. A total of 59 "alcoholic" patients were diagnosed and only one patient relapsed when properly diagnosed with the kit and psychosocial interview. Treatment is obviously oriented around the proper diagnosis and appropriate psychobiological treatment is then being undertaken.

TABLE 1

| ALCOHOLIC PATIENTS | | | | | | | | | |
|---|---|---|---|---|---|---|---|---|---|
| | ACODES | SUBSTANCE | AAGE | AT | ATH | ATS | AB | AWBC | ALYM |
| CASE 1 | P5003 | Alcohol | 52 | 1971 | 1609 | 320 | 384 | 7400 | 3552 |
| CASE 2 | P5004 | Mixed | 24 | 1035 | 795 | 276 | 206 | 5100 | 1623 |
| CASE 3 | P5007 | Cocaine | 36 | 1375 | 1135 | 291 | 133 | 7600 | 2052 |
| CASE 4 | P5002 | Alcohol | 37 | 636 | 799 | 169 | 34 | 5500 | 1485 |
| CASE 5 | P5011 | Mixed | 29 | 917 | 732 | 169 | 93 | 8800 | 1496 |
| CASE 6 | P5002 | Alcohol | 37 | 1300 | 919 | 346 | 118 | 7400 | 2368 |
| CASE 7 | P5004 | Mixed | 24 | 1529 | 1326 | 433 | 119 | 10300 | 2987 |
| CASE 8 | P5011 | Mixed | 29 | 778 | 600 | 230 | 71 | 11300 | 1243 |
| CASE 9 | P5007 | Cocaine | 36 | 1108 | 1032 | 264 | 98 | 6500 | 1820 |
| CASE 10 | P5015 | Heroin | 16 | 1847 | 872 | 419 | 170 | 6000 | 2700 |
| CASE 11 | P5003 | Alcohol | 52 | 1354 | 1357 | 254 | 138 | 6300 | 2331 |
| CASE 12 | P5017 | Mixed | 35 | 1082 | 680 | 386 | 88 | 8000 | 1600 |
| CASE 13 | P5023 | Alcohol | 55 | 1378 | 1009 | 383 | 99 | 6000 | 1740 |
| CASE 14 | P5002 | Alcohol | 37 | 1100 | 860 | 319 | 103 | 6400 | 1664 |
| CASE 15 | P5002 | Alcohol | 37 | 1121 | 938 | 291 | 193 | 6100 | 1891 |
| CASE 16 | P5003 | Alcohol | 52 | 1384 | 930 | 372 | 116 | 5000 | 2000 |
| CASE 17 | P5033 | Alcohol | 26 | 1250 | 788 | 466 | 204 | 5000 | 2100 |
| CASE 18 | P5034 | Mixed | 34 | 620 | 355 | 304 | 12 | 7200 | 1008 |
| CASE 19 | P5002 | Alcohol | 37 | 1074 | 817 | 303 | 84 | 6800 | 1836 |
| CASE 20 | P5004 | Mixed | 24 | 1321 | 1078 | 277 | 171 | 7600 | 1824 |
| CASE 21 | P5039 | Cocaine | 41 | 852 | 514 | 339 | 92 | 7900 | 1027 |
| CASE 22 | P5039 | Cocaine | 41 | 1106 | 620 | 419 | 78 | 7900 | 1501 |
| CASE 23 | P5040 | Mixed | 44 | 2136 | 1823 | 438 | 114 | 7900 | 2844 |
| CASE 24 | P5044 | Mixed | 20 | 2060 | 1816 | 509 | 97 | 9800 | 2842 |
| CASE 25 | P5002 | Alcohol | 37 | 1127 | 933 | 250 | 190 | 6400 | 1728 |
| CASE 26 | P5034 | Mixed | 34 | 1306 | 749 | 607 | 33 | 7900 | 1817 |
| CASE 27 | P5041 | Mixed | 11 | 1538 | 1180 | 527 | 169 | 4300 | 2107 |
| TOTAL OBSERVATIONS: 27 | | | | | | | | | |

| | AAGE | AT | ATH | ATS | AB | AWBC | ALYM |
|---|---|---|---|---|---|---|---|
| N OF CASES | 27 | 27 | 27 | 27 | 27 | 27 | 27 |
| MINIMUM | 11 | 620 | 355 | 169 | 12 | 4300 | 1008 |
| MAXIMUM | 55 | 2136 | 1823 | 607 | 384 | 11300 | 3552 |
| MEAN | 35 | 1271 | 973 | 347 | 126 | 7126 | 1970 |
| STANDARD DEV | 11 | 392 | 361 | 106 | 73 | 1650 | 605 |

A = Alcoholic
B = Borderline
C = Control
T = $CD_3$
TH = $CD_4$
TS = $CD_8$
B = $CD^{19}$
WC = White Blood Count
LYM = Total Lymphocyte Count

TABLE 2

| CONTROL SUBJECTS | | | | | | | |
|---|---|---|---|---|---|---|---|
| | CCODES | CAGE | CT | CTH | CTS | CB | CWBC | CLYM |
| CASE 1 | C1003 | 26 | 2054 | 1017 | 864 | 120 | 7900 | 3239 |

TABLE 2-continued

| CONTROL SUBJECTS | | | | | | | | |
|---|---|---|---|---|---|---|---|---|
| CASE 2 | C1002 | 39 | 1892 | 1456 | 576 | 416 | 12500 | 4000 |
| CASE 3 | C1005 | 24 | 1394 | 670 | 416 | 135 | 5400 | 2106 |
| CASE 4 | C5006 | 24 | 1780 | 958 | 852 | 65 | 6300 | 2583 |
| CASE 5 | C1003 | 26 | 1642 | 693 | 550 | 118 | 8100 | 2349 |
| CASE 6 | C5008 | 19 | 2244 | 1343 | 773 | 250 | 7500 | 3375 |
| CASE 7 | C5009 | 22 | 3006 | 1770 | 1079 | 378 | 7500 | 4350 |
| CASE 8 | C5010 | 51 | 3066 | 2134 | 671 | 186 | 7400 | 4218 |
| CASE 9 | C5012 | 25 | 1597 | 1117 | 555 | 150 | 6700 | 2412 |
| CASE 10 | C5021 | 34 | 2173 | 1327 | 866 | 159 | 9400 | 3384 |
| CASE 11 | C5022 | 32 | 1845 | 1277 | 794 | 120 | 6800 | 2856 |
| CASE 12 | C5024 | 5 | 2191 | 1397 | 1111 | 226 | 6700 | 3484 |
| CASE 13 | C5029 | 45 | 2415 | 1402 | 934 | 180 | 7700 | 3157 |
| CASE 14 | C5032 | 30 | 2229 | 1582 | 776 | 141 | 7000 | 2940 |
| CASE 15 | C1006 | 41 | 1360 | 1147 | 415 | 91 | 4700 | 1974 |
| CASE 16 | C1007 | 36 | 1476 | 949 | 561 | 86 | 4600 | 1794 |
| CASE 17 | C1002 | 39 | 1610 | 1288 | 501 | 203 | 8600 | 2666 |
| CASE 18 | C1005 | 24 | 2528 | 1209 | 862 | 169 | 5900 | 3304 |
| CASE 19 | C1012 | 23 | 2572 | 1981 | 861 | 159 | 8800 | 3696 |
| CASE 20 | C5036 | 26 | 1174 | 933 | 742 | 137 | 9100 | 2275 |
| CASE 21 | C5036 | 26 | 1820 | 1471 | 609 | 335 | 9100 | 2912 |
| CASE 22 | C1021 | 37 | 1617 | 911 | 625 | 85 | 8800 | 2024 |
| CASE 23 | C1022 | 37 | 1309 | 824 | 707 | 180 | 6600 | 1980 |
| TOTAL OBSERVATIONS: 23 | | | | | | | | |

| | CAGE | CT | CTH | CTS | CB | CWBC | CLYM |
|---|---|---|---|---|---|---|---|
| N OF CASES | 23 | 23 | 23 | 23 | 23 | 23 | 23 |
| MINIMUM | 5 | 1174 | 670 | 415 | 65 | 4600 | 1794 |
| MAXIMUM | 51 | 3066 | 2134 | 1111 | 416 | 12500 | 4350 |
| MEAN | 30 | 1956 | 1255 | 726 | 178 | 7526 | 2916 |
| STANDARD DEV | 10 | 521 | 379 | 190 | 91 | 1737 | 746 |

TABLE 3

| BORDERLINE PERSONALITY PATIENTS | | | | | | | | |
|---|---|---|---|---|---|---|---|---|
| | BPCODES | SUBSTANCE | BPAGE | BPT | BPTH | BPTS | BPB | BPWBC | BPLYM |
| CASE 1 | P5005 | Alcohol | 23 | 1712 | 484 | 785 | 128 | 5000 | 2200 |
| CASE 2 | P5005 | Alcohol | 23 | 1494 | 976 | 582 | 88 | 7400 | 2146 |
| CASE 3 | P5005 | Alcohol | 23 | 2123 | 1132 | 805 | 275 | 6700 | 2747 |
| CASE 4 | P5018 | Cocaine | 50 | 1755 | 974 | 798 | 162 | 10000 | 2900 |
| CASE 5 | P5025 | Alcohol | 26 | 2870 | 1759 | 1225 | 114 | 11500 | 3680 |
| CASE 6 | P5026 | Cocaine | 23 | 2802 | 1765 | 892 | 87 | 12500 | 3625 |
| CASE 7 | P5001 | Mixed | 18 | 2838 | 1694 | 1274 | 327 | 7800 | 3588 |
| CASE 8 | P5030 | Mixed | 57 | 2753 | 488 | 864 | 68 | 5700 | 2280 |
| CASE 9 | P5031 | Mixed | 28 | 3007 | 1853 | 1332 | 492 | 9400 | 4136 |
| CASE 10 | P5035 | Heroin | 38 | 2621 | 1443 | 959 | 70 | 7900 | 3476 |
| CASE 11 | P5035 | Heroin | 38 | 1842 | 1345 | 618 | 63 | 8700 | 2523 |
| CASE 12 | P5036 | Amphetamines | 26 | 1820 | 1471 | 609 | 335 | 9100 | 2912 |
| CASE 13 | P5047 | Cocaine | 26 | 2094 | 1304 | 1064 | 309 | 7800 | 3432 |
| CASE 14 | P5049 | Alcohol | 18 | 3276 | 2016 | 1296 | 144 | 7500 | 3600 |
| CASE 15 | P5050 | Alcohol | 37 | 2275 | 1334 | 927 | 225 | 6600 | 2970 |
| CASE 16 | P5051 | Alcohol | 44 | 2453 | 1579 | 696 | 208 | 8400 | 3360 |
| TOTAL OBSERVATIONS: 16 | | | | | | | | | |

| | BPAGE | BPT | BPTH | BPTS | BPB | BPWBC | BPLYM |
|---|---|---|---|---|---|---|---|
| N OF CASES | 16 | 16 | 16 | 16 | 16 | 16 | 16 |
| MINIMUM | 18 | 1494 | 484 | 582 | 63 | 5000 | 2146 |
| MAXIMUM | 57 | 3276 | 2016 | 1332 | 492 | 12500 | 4136 |
| MEAN | 31 | 2358 | 1351 | 920 | 193 | 8250 | 3098 |
| STANDARD DEV | 12 | 542 | 451 | 252 | 125 | 1966 | 602 |

It is intended that the foregoing description be only illustrative of the present invention and that the present invention be limited only by the hereinafter appended claims.

I claim:

1. A method for diagnosing an inherited substance abuse dependency in humans which comprises:
   (a) drawing a sample of peripheral blood from a human who is in good health except for a possible inherited substance abuse dependency;
   (b) separating white cells from the blood containing T-cell lymphocytes including CD-8 T-cell suppressor cells; and
   (c) determining a number of the CD8 T-cell suppressor cells in the white cells by counting wherein the human with the inherited substance abuse dependency has a reduced CD8 T-cell suppressor cell number below about 500 cells per microliter of the sample of blood as compared to humans without the dependency.

2. The method of claim 1 wherein the CD8 T-cell suppressor cells are fluorescently labeled for counting and counted.

3. The method of claim 1 wherein a labeled antibody for the CD8 T-cell suppressor cells is reacted with the CD8 T-cell suppressor cells and then the label is sued to determine the number of the CD8 T suppressor cells.

4. The method of claim 3 wherein the antibody is labeled with an fluorescent compound.

5. The method of claim 3 wherein the antibody is a monoclonal antibody which reacts with the CD8 T-cell suppressor cells.

6. The method of claim 1 wherein in separating the white cells from the blood a whole lymphocyte preparation is lysed to eliminate the non-lymphatic cells.

7. The method of claim 6 wherein an antibody labeled with an fluorescent compound is provided and reacted with the CD8 T-cell suppressor cells in the separated T-cell lymphocytes so as to stain the CD8 T-cell suppressor cells to determine the number of the CD8 T-cell suppressor cells.

8. The method of claim 7 wherein the number of CD8 T-cell suppressor cells is determined with a flow cytometer or a microscope.

9. A method for diagnosing an inherited substance abuse dependency in human which comprises:
 (a) determining a number of CD-8 T-cell suppressor cells in white cells in a peripheral blood sample of a human subject who is in good health except for possible inherited substance abuse dependency; and
 (b) comparing the T-cell suppressor cells of the subject to the T-cell suppressor cells of a human without a substance abuse dependency and with normal numbers of T-cell suppressor cells by counting to determine whether the human subject has a reduced T-cell suppressor cell number below about 500 cells per microliter of the sample of blood and thus the inherited substance abuse dependency.

* * * * *

UNITED STATES PATENT AND TRADEMARK OFFICE
CERTIFICATE OF CORRECTION

PATENT NO. : 5,081,011

DATED : January 14, 1992

INVENTOR(S) : Ronald H. Bradley

It is certified that error appears in the above-identified patent and that said Letters Patent is hereby corrected as shown below:

Column 1, line 7, "and", second occurrence, should be --an--.

Column 2, line 10, "97:153-167) 1988." should read --97:153-167, 1988.--.

Column 2, line 17, "13:786-789) 1989." should read --13:786-789, 1989--.

Column 4, line 33, "an" should be --any--.

Column 7, line 42, "$CD_4$" should be --CD4--.

Column 9, line 64, "$B=CD^{19}$", should be --$B=CD_{19}$--.

Column 12, line 65, "sued" should be --used--.

Signed and Sealed this

Sixth Day of July, 1993

*Attest:*

MICHAEL K. KIRK

*Attesting Officer*  *Acting Commissioner of Patents and Trademarks*